United States Patent [19]

Tarrson et al.

[11] Patent Number: 4,947,880
[45] Date of Patent: Aug. 14, 1990

[54] DENTAL FLOSSING DEVICE

[75] Inventors: Emanuel B. Tarrson; Dane Maric, both of Chicago, Ill.

[73] Assignee: John O. Butler Company, Chicago, Ill.

[21] Appl. No.: 224,668

[22] Filed: Jul. 27, 1988

[51] Int. Cl.$^5$ .............................................. A61C 15/00
[52] U.S. Cl. ..................................... 132/329; 132/321
[58] Field of Search ............... 132/321, 323, 329, 325; 223/102

[56] References Cited

U.S. PATENT DOCUMENTS

| | | | |
|---|---|---|---|
| 1,839,486 | 1/1932 | Lawton | 132/323 |
| 1,863,717 | 6/1932 | Holden | 223/102 |
| 2,522,794 | 9/1950 | Medof | 132/325 |
| 3,896,824 | 7/1975 | Thornton | 132/321 |
| 3,930,059 | 12/1975 | Wells | 132/321 |
| 4,011,658 | 3/1977 | Tarrson et al. | 433/216 |
| 4,215,478 | 8/1980 | Thomas et al. | 132/323 |
| 4,364,380 | 12/1982 | Lewis | 132/321 |
| 4,465,462 | 8/1984 | Ticknor | 433/136 |
| 4,519,408 | 5/1985 | Charaton | 132/321 |
| 4,523,600 | 6/1985 | Donovan | 132/321 |
| 4,832,063 | 5/1989 | Smole | 132/321 |

*Primary Examiner*—Cary E. Stone
*Attorney, Agent, or Firm*—Laff, Whitesel, Conte & Saret

[57] ABSTRACT

A dental flossing cord is made from only a single kind of material. The inventive cord has a leader portion which is created by causing the multi-strands of the cord to cling together in a unified mass, preferably by an ultrasonic heat treatment which welds the strands together. The invention is especially useful on osseointegrated implant pillars.

18 Claims, 1 Drawing Sheet

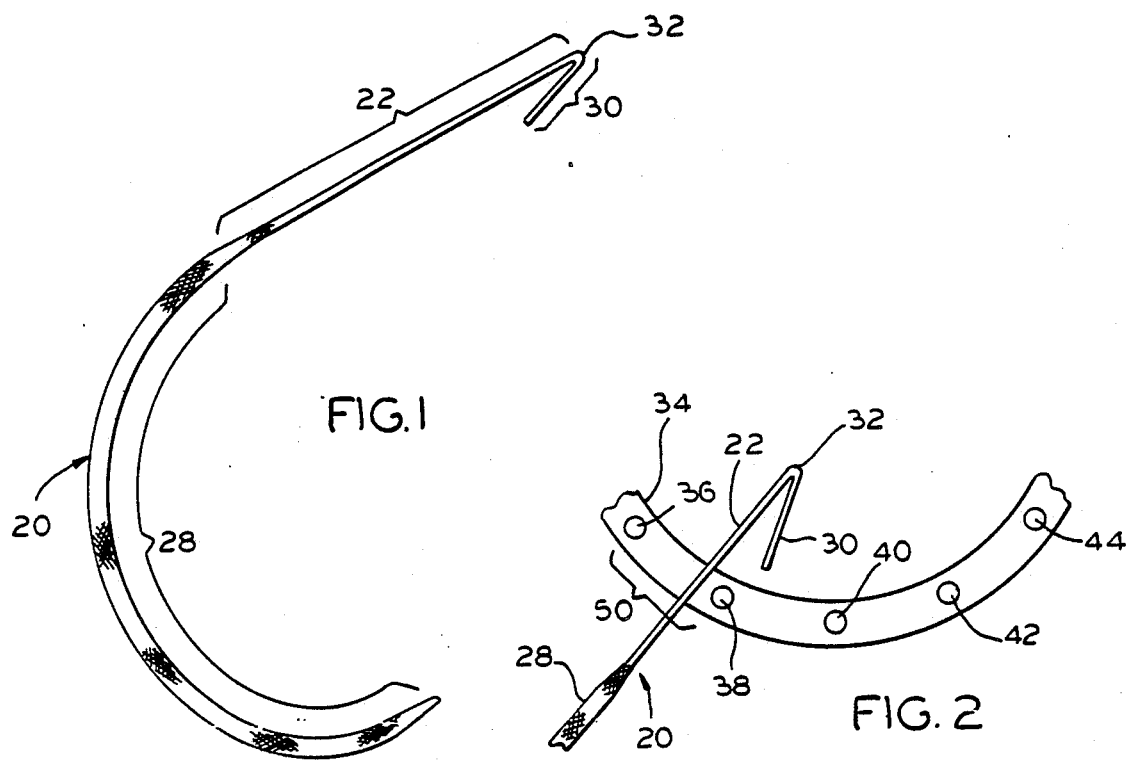
FIG. 1
FIG. 2
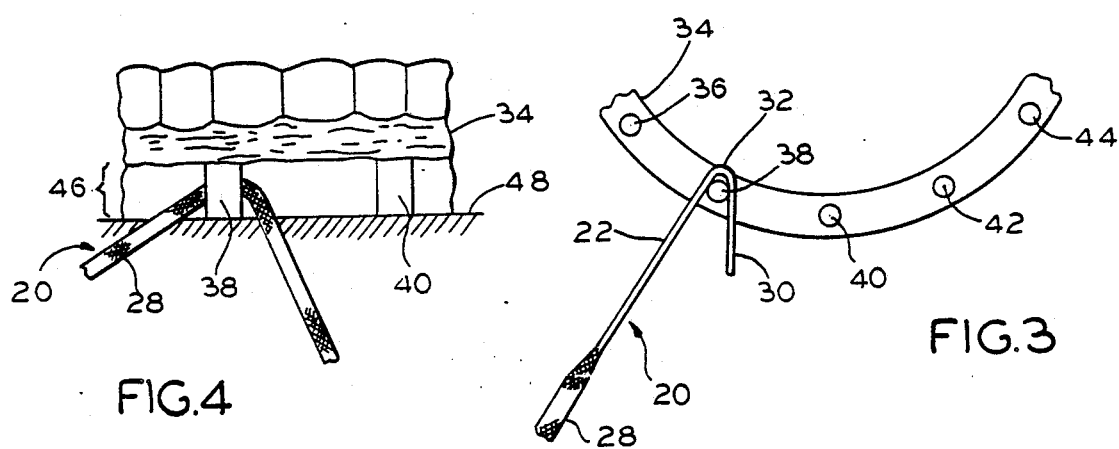
FIG. 4
FIG. 3
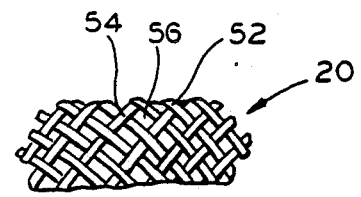
FIG. 5

DENTAL FLOSSING DEVICE

This invention relates to dental flossing devices and more particularly to such devices having an integral flosser cord and threader.

The familiar and well known dental floss is merely a thread which is simply and directly passed into the interdental space between the teeth and then moved back and forth. This flossing method is completely satisfactory as long as there are no obstructions to fitting the floss into the interdental space between the teeth.

There are many well-known devices for threading floss when the simple and direct method of insertion into interdental space is not possible. For example, a floss threader may be used to thread dental floss under a bridge which is attached to and spans the space between adjacent teeth, as where the bridge may replace an extracted molar.

These known floss threaders do not function as well as they could when used with an osseointegrated implant or fixed bridge. This kind of implant is usually mounted on the top of titanium pillars which are permanently implanted in the jaw bone. The pillars provide a small space between the top of the gum and the bottom of the bridge. If the pillars are not thoroughly cleaned, they are likely to collect plaque and calculus which may inflame the gum and possibly lead to an erosion of the jawbone in which the titanium pillars are anchored.

Normal and known dental floss and threading devices are not always entirely satisfactory for cleaning these pillars. Therefore, a multi-strand floss cord has been developed wherein a plurality of monofilament strands are woven into a tubular cord, which can be in the nature of one millimeter in diameter or other suitable diameter. This kind of cord is threaded around, behind the pillars and then pulled back and forth. Each strand in the cord rubs against the back of the pillar to clean and polish the surface thereof.

A known device has solved the problem of threading the dental floss cord around the osseointegrated implant pillar by providing a monofilament leader which is bent back upon itself, thereby forming a permanent hook on one end. The other end of the monofilament leader is cemented to an end of the dental flossing cord. To insert the flossing cord, the hook end is passed into a space between the pillars and between the upper surface of the gum and the lower surface of the dentures affixed to the pillars. Then, the hook is pulled back so that the free end of the hook encircles a pillar, with the free end emerging on an opposite side of the pillar. The free end is grasped and pulled. The dental flossing cord follows the leader around the post and arrives in a flossing position.

The difficulty which has been experienced with this kind of a flossing cord occurs at the point where the monofilament leader is cemented to the flossing cord. The cement must not only be attached to the cord in a manner which insures a smooth dimensional transition from the diameter of the monofilament to the diameter of the cord, but which also meets and receives FDA approval. A cement which meets FDA approval may release the cord from the leader or form an obstacle that may snag as the dental flossing cord enters a small interdental space while it follows the monofilament leader. At the present time, a cement which solves the mechanical problems has not received FDA approval.

Accordingly, an object of the invention is to provide a new and improved dental flossing cord. Here, an object is to provide such a flossing cord which does not include any material other than that of the flossing cord itself. In this connection, an object is to provide a dental flossing cord which is shaped to form its own leader.

Another object of the invention is to provide a dental flossing cord which, on one end, is reduced in diameter, made relatively stiff, and formed into a threading hook.

Still another object is to provide a dental flossing cord which does not require any non-FDA approved substance. In particular, an object is to provide a dental flossing cord which does not require cement or another bonding agent.

In keeping with an aspect of the invention, these and other objects are accomplished by providing a dental flossing cord which has been heat, or otherwise, treated on one end portion. The treatment shrinks the end portion diameter of the cord, makes it relatively stiff, and gives it a permanent geometrical shape of a hook. The hook is inserted into a space adjacent the pillar and then pulled back to hook around the pillar. Then, the end of the hook is pulled, the dental flossing cord following around a pillar of an osseointegrated implant.

For convenience of expression, the following specification refers to a "heat treatment" which is used to reduce the diameter of the dental flossing cord on one end portion in order to form a leader section. However, it should be understood that the objective of the treatment process is to unify a plurality of cord strands into an integral and coherent mass. Any suitable treatment process which makes the strands stick together in such an integral and coherent mass and which forms a leader, falls within the general scope of the invention. Therefore, the appended claims should cover all equivalent structures and treatments.

A preferred embodiment for accomplishing these and other objects is shown in the attached drawings, wherein:

FIG. 1 shows the inventive dental flossing cord;

FIG. 2 schematically illustrates a first step in threading the dental flossing cord around an implant pillar;

FIG. 3 is a view similar to FIG. 2, but with the hook of the cable tie leader in place around an implant pillar;

FIG. 4 is a schematic view of an osseointegrated fixed bridge with an implant pillar being flossed; and FIG. 5 is a fragment of the flossing dental cord, greatly enlarged, to show the strands from which the cord was woven.

The inventive dental flossing cord 20 is seen in FIG. 1 as including a single length of a multi-strand cord which may be in the order of approximately ten to fifteen inches long, the outside tube diameter being approximately a millimeter. The cord is a tube made by weaving a plurality of monofilament strands. The last three or four inches 22 of the dental flossing cord 20 is given a heat or other treatment which significantly compresses or shrinks the diameter of the cord to about one-half to two-thirds of a millimeter and makes it relatively stiff. The remaining portion 28 of the dental flossing cord has an unreduced cross section which is not affected by the heat treatment.

During this heat or other treatment process, the end of the cord is formed into a hook by being bent back upon itself by an end portion 30 which is approximately three-quarters of an inch long. The bending back forms a somewhat rounded point 32 which may be inserted into interdental spaces and a gap near an implant pillar.

FIG. 2 schematically shows a denture plate 34 which is attached to a human jaw by five pillars 36–44 which are permanently implanted in a human jaw bone. As seen in FIG. 4, there is a space 46 between the denture plate 34 and the gum surface 48 of the jaw.

The point 32 of the dental flossing leader portion 22 is passed into the space between pillars 36, 38 (FIGS. 2, 3). After the bent back portion 30 passes behind the pillar 38, it is grasped and pulled, the leader portion 22 passing around the pillar 38 without pulling the dental flossing cord portion 28 after it. Once the dental flossing cord 20 is in place (FIG. 4), its opposite ends are pulled back and forth, thereby cleaning and burnishing the back of the pillar.

FIG. 5 shows the weave of the dental flossing cord 20 as including a plurality of monofilament strands, two of which are numbered 52, 54. Each strand presents a separate surface for rubbing and burnishing the pillar. The interstices (such as 56) between each of the adjacent strands provide space for collecting debris. The dental flossing cord 20 has FDA approval. The leader portion 22, 30 and the remainder 28 of the cord 20 are the same approved material.

The heat or other treatment may take any of many different forms and processes. However, the preferred process uses ultrasonic energy to heat the cord strands, which are preferably made of nylon, and to partially melt them to the extent that they weld together to make a unified and integrated mass.

An advantage of the invention is that there is no separate leader or cement made of non-FDA-approved material. Moreover, the heat or other treatment which reduces the diameter of the dental flossing cord to produce the leader portion 22 also produces a gradual thinning of the cord in the area 58 (FIG. 1). Thus, there is no abrupt discontinuity of diameter between the leader and the dental cord to snag at an entrance to a space through which the leader is being threaded.

Those who are skilled in the art will readily perceive how to modify the invention. Therefore, the appended claims are to be construed to cover all equivalent structures which fall within the true scope and spirit of the invention.

The claimed invention is:

1. A dental flossing device comprising a woven multistrand flossing cord having a first diameter and made of a material which can be shrunk and made stiffer, one end portion of said cord being so shrunken and made stiffer as to form a leader having a diameter which is less than said first diameter, and an end section of said end portion being bent back upon itself to form a hook.

2. The dental flossing device of claim 1 wherein said end section is long enough to pass behind an object in the oral cavity and emerge on the other side of said object to be grasped and pulled through a space associated with human teeth.

3. The dental flossing device of claim 2 wherein said multi-strands are shrunken and made stiffer responsive to heating said one end portion of said cord in order to form said leader.

4. The dental flossing of claim 3 wherein said heating of said one end portion of said cord is accomplished by ultrasonic energy.

5. The dental flossing of claim 3 wherein said heating of said cord produces a progressively increased amount of shrinking at the junction between a cord portion having an unreduced diameter and said leader in order to produce a gradual reduction in said diameter.

6. A unitary one-piece dental flossing cord made exclusively of monofilament fibers, said cord being woven from a plurality of individual monofilament strands, said woven cord having physical dimensions and the physical dimensions being compressed in an end portion of said cord to form it into a leader of a diameter which is reduced with respect to a diameter of said woven cord, said strands in said end portion sticking together in a unified mass after said compression and without an addition of any other material to said monofilament, and an end section of said end portion being permanently shaped to bend back upon itself to form a hook on an end of said unified mass, said end section of said hook being long enough to thread said leader through spaces in the dental area of the mouth.

7. A dental flosser made exclusively of one kind of material which shrinks and bonds to itself when it is heated, said flosser comprising said material formed into an elongated device having a plurality of rubbing surfaces separated by interstices for collecting debris rubbed off an object in the dental area of a mouth, an end portion of said device being heat shrunken and bonded into a coherent mass which is stiff enough and thin enough to act as a leader for threading said elongated device within said dental area, and means forming an end section of said end portion into a permanent geometric hook shape which facilitates a threading of said leader.

8. The dental flosser of claim 7 wherein said object in said dental area is an implant pillar which supports an artificial dental structure.

9. The dental flosser of claim 8 wherein said geometric shape enables said leader to reach around and to emerge from behind said pillar.

10. The dental structure of claim 9 wherein said geometrical shape is formed by said end section having been bent back upon itself to form a somewhat rounded, pointed part.

11. A dental flossing cord made solely of multistrands of a single material which is woven to form a tube, the strands on a portion of said cord being separate from each other to form a plurality of rubbing surfaces with the space between the strands forming interstices for collecting debris rubbed off an object in an oral cavity, the strands on a second portion of said cord being integrated into a mass of strands which have been welded together and shrunken to form a leader portion of reduced diameter, and the end of said leader portion being permanently formed to fold back upon itself to form a hook having a somewhat pointed end, said point fitting through a first space and returning through a second space associated with a denture support.

12. The cord of claim 11 wherein said tube is about one millimeter in diameter.

13. The cord of claim 12 wherein the folded back end is in the order of approximately three-quarters to one inch long.

14. The cord of claim 12 wherein said cord in the area of said integrated mass forming said leader portion is in the order of one-half to two-thirds of a millimeter in diameter.

15. The end of claim 11 wherein the folded back end of said leader is approximately one-third of the total length of the leader.

16. A dental flossing cord made solely of multistrands woven to form a tube, said tube being about one millimeter in diameter, the strands on a portion of said cord being separate from each other to form a plurality of rubbing surfaces with the space between the strands forming interstices for collecting debris rubbed off an object in an oral cavity, the strands on a second portion of said cord being integrated into a mass of strands which cling together to form a leader portion, said cord in the area of said integrated mass forming said leader portion being in the order of one-half to two-thirds of a millimeter in diameter, said cord having a substantially smooth taper in the region between the one millimeter diameter and the one-half to two-thirds diameter, and the end of said leader port in folding back upon itself to form a point.

17. The cord of claim 16 wherein said tube is in the order of approximately ten to fifteen inches long.

18. The cord of claim 16 wherein said leader portion is in the order of approximately two to three inches long.